United States Patent [19]

Ogawa et al.

[11] Patent Number: 4,722,777

[45] Date of Patent: Feb. 2, 1988

[54] IMPROVEMENT OF ELECTROPHORETIC ELEMENT USING POLYACRYLAMIDE GEL

[75] Inventors: Masashi Ogawa; Hideo Matsunaga, both of Asaka; Yukio Shinagawa, Minami-ashigara, all of Japan

[73] Assignee: Fuji Photo Film Co., Ltd., Kanagawa, Japan

[21] Appl. No.: 903,884

[22] Filed: Sep. 3, 1986

Related U.S. Application Data

[63] Continuation of Ser. No. 750,886, Jul. 1, 1985, abandoned.

[30] Foreign Application Priority Data

Jun. 30, 1984 [JP] Japan ................................. 59-136247
Jun. 30, 1984 [JP] Japan ................................. 59-136248

[51] Int. Cl.$^4$ ...................... C25D 13/02; C25D 13/08
[52] U.S. Cl. .............................. 204/299 R; 204/182.7; 204/182.8
[58] Field of Search ............. 204/299 R, 182.8, 182.7; 524/555, 850; 428/477.7

[56] References Cited

U.S. PATENT DOCUMENTS 3,875,044  4/1975  Renn et al. ...................... 204/299 R
3,922,432  11/1975  Renn .................................... 428/327
3,960,499  6/1976  White .................................... 422/55
4,415,428  11/1983  Nochumson et al. .......... 204/299 R

*Primary Examiner*—John F. Niebling
*Assistant Examiner*—Nam X. Nguyen
*Attorney, Agent, or Firm*—Jules E. Goldberg

[57] ABSTRACT

An element for electrophoresis suitably employable for analysis of biopolymers such as proteins, as well as for determination of base sequence of DNA, RNA, their fragments, and their derivatives, which comprises a plastic material support, an adhesive layer containing an inorganic oxide and a binder, a medium layer for electrophoresis comprising an aqueous polyacrylamide gel formed by crosslinking polymerization of an acrylamide compound and a crosslinking agent in the presence of water, and a plastic material covering film. The electrophoresis medium layer may contain a water-soluble polymer and agarose. The medium layer may contain a modifier such as an anionic surfactant, formamide or urea.

22 Claims, No Drawings

IMPROVEMENT OF ELECTROPHORETIC ELEMENT USING POLYACRYLAMIDE GEL

This is a continuation of application Ser. No. 750,886, filed July 1, 1985 now abandoned.

BACKGROUND OF THE INVENTION

1. Field of the Invention

This invention relates to an element for electrophoresis, and more particularly relates to an element for electrophoresis suitably employable for analysis of biopolymers such as proteins, as well as for determination of base sequence of DNA, RNA, their fragments, and their derivatives.

2. Description of Prior Arts

For the analysis of biopolymers such as proteins, or for the determination of base sequence of DNA or RNA, the electrophoresis can be carried out in the following manner.

A membrane medium for electrophoresis prepared by coating or casting a membrane-forming material, such as, agar, cellulose, cellulose acetate, starch, silica gel or polyacrylamide gel over a support, such as, a glass plate or a transparent plastic sheet (or film) is impregnated with a buffer solution; on the medium is applied a substance to be analyzed (sample); the applied sample is developed (or resolved) on or in the medium by applying a voltage between both ends of the support; the developed substance is dyed thereon; and then the dyed sample is measured on the optical density to quantitatively determine the developed components of the sample.

Details of the electrophoresis and medium therefor are given in "Experimental Text for Electrophoresis (5th revision)" edited by Electrophoresis Society of Japan (Bunkodo, 1975), "Modern Electrophoresis" edited by Aoki & Nagai (Hirokawa Shoten, 1973), etc.

Recently, the electrophoresis has been frequently employed to analyze substances originating from a living body; for instance, the analyses of proteins originating from a living body are generally performed in the course of biochemical analysis for diagnosis. The determinations of base sequences of DNA or RNA are also performed in the course of the study in the genetic engineering technology.

As the membrane or sheet for electrophoresis, a filter paper was previously employed, but recently an agarose membrane or a polyacrylamide gel membrane (or medium) has been employed from the viewpoints of their advantageous properties. Particularly, the polyacrylamide gel membrane showing a molecular sieve function is widely employed recently. More particularly, in the method for determination of base sequence of DNA, RNA, their fragments, and their derivatives according to the post-label method, a procedure of slab electrophoresis using a polyacrylamide gel membrane has become essential.

The polyacrylamide gel membrane can be prepared by crosslinking polymerization of a monomer such as acrylamide and a two-functional crosslinking agent such as N,N'-methylenebisacrylamide under an oxygen-free condition in the presence of water and a polymerization catalyst. In the course of the preparation of the polyacrylamide gel membrane, a modifier such as an anionic surfactant, urea or formamide is incorporated into the membrane in certain cases.

Since the polymerization reaction for the preparation of polyacrylamide is a radical crosslinking polymerization as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a crosslinking agent and a polymerization catalyst into a cell formed between two glass plates with a certain clearance (e.g., 0.3–1 mm); sealing the gel-forming solution from oxygen; and causing the crosslinking polymerization to prepare the desired gel membrane.

The polyacrylamide gel membrane prepared as above is employed for electrophoresis. For example, the electrophoresis for analysis of biopolymers such as proteins is performed in the manner such as described below.

The prepared polyacrylamide gel is horizontally or vertically placed for performing slab electrophoresis. The electrophoresis is performed for a certain period of time under predetermined conditions, and the desired analysis of the components originating from the living body is done after dyeing the electrophoresed gel membrane with, for instance, Ponceau 3R (Ciba-Geigy), Coomassie Brilliant Blue G-250 (ICI), or silver.

Since the study in the genetic engineering technology has advanced recently, quick determination of the base sequence of DNA, etc. is highly desired. The polyacrylamide gel membrane prepared as above is also employed for electrophoresis for determination of base sequence of DNA in the manner such as described below.

The polyacrylamide gel membrane is vertically placed in the form of being sandwiched between the glass plates, and in the first place a pre-electrophoresis procedure is carried out. Then, a certain amount of a sample (e.g., $^{32}$p-labeled DNA cleaved by Maxam-Gilbert method) is introduced into sample slots provided on the membrane, and electrophoresis is carried out. After the electrophoresis is carried out for a certain period of time (e.g., approx. 6–12 hours), one glass plate is removed carefully. Then, the exposed gel membrane is covered with a polymer film such as a poly(vinylidene chloride) film and subjected to the autoradiographic process. The autoradiographic process is carried out by the following procedures: A radiographic film and an intensifying screen are superposed successively on the film covering the gel membrane, whereby exposing the radiographic film to the gel membrane at a low temperature (e.g., $-80°$ C.) for a certain period of time (e.g., approx. 10–20 hours). After the exposing procedure, the radiographic film is developed, and the resolved pattern reproduced on the film is studied for determination of the base sequence of DNA, etc.

Since the autoradiographic process requires a long period as described above, it has been desired that the operational period is shortened. Moreover, enhancement of resolution accuracy in the detection of the resolved pattern is desired.

The above procedures employing glass plates are disadvantageous because the glass plate is easily breakable and rather heavy and careful handling is accordingly required. Thus, those procedures employing the glass plates ae difficultly utilized to prepare the polyacrylamide gel membrane in a mass scale.

For the reason described above, it has been desired that the glass plate for supporting the polyacrylamide gel membrane is replaced with a light-weight plastic material support such as a polyethylene terephthalate (PET) sheet. However, in spite of the use of a plastic material support, poor adhesion between the gel membrane and the plastic material support should be improved, because such plastic material supports are usually hydrophobic. Even if the surface of the plastic material support is made hydrophilic, or if the hydrophilic plastic material support is used, the adhesion between the gel membrane and the plastic material support is not at a satisfactory level.

The gel membrane is apt to separate from the support in the above procedure even in the case of employing the glass plate support. Therefore, these procedures require highly skilled operation to prevent the separation of the gel membrane from the support. The poor affinity of the plastic material support to the polyacrylamide gel membrane makes it more difficult to handle the element for electrophoresis without separation of the support from the gel membrane.

SUMMARY OF THE INVENTION

An object of the present invention is to provide an element for electrophoresis which is improved in the adhesion between the plastic material support (plastic film or sheet) and the electrophoresis medium layer (polyacrylamide gel membrane).

Another object of the present invention is to provide an element for electrophoresis which is substantially free from separation of the electrophoresis medium layer from the support in the following stages such as a post-treatment stage in an aqueous solution and a subsequent drying stage.

The first embodiment of the present invention is an element for electrophoresis comprising:

(I) a plastic material support;
(II) an adhesive layer containing an inorganic oxide and a binder;
(III) a medium layer for electrophoresis comprising an aqueous polyacrylamide gel formed by crosslinking polymerization of an acrylamide compound and a crosslinking agent in the presence of water; and
(IV) a plastic material covering film;

which are superposed in this order.

The adhesive layer containing an inorganic oxide and a binder may be provided on the medium layer instead of on the plastic material support (the second embodiment of the present invention).

The adhesive layer may also be provided both on the plastic material support and on the medium layer (the third embodiment of the present invention).

The element for electrophoresis of the invention is highly resistant to separation between the support layer and the electrophoresis medium layer in a variety of the stages. Accordingly, the medium layer is hardly broken in the analytical procedure, and the handling of the element is satisfactorily easy.

Moreover, the electrophoresis element of the invention can be prepared by forming the medium layer on an adhesive layer which is formed on a horizontally arranged plastic material support or plastic material covering film. Therefore, the element for electrophoresis of the invention can be advantageously prepared on a mass scale.

DETAILED DESCRIPTION OF THE INVENTION

The support of the element for electrophoresis according to the present invention is a plastic material support. The plastic material support includes a variety of polymer materials in the form of sheet (the term "sheet" includes a film and a plate). Examples of the polymer materials include polyethylene terephthalate, polycarbonate of Bisphenol A, polyvinyl chloride, vinylidene chloride—vinyl chloride copolymer, polymethyl methacrylate, polyethylene, polypropylene, cellulose acetates, and cellulose acetate propionate. Preferred is a polyethylene terephthalate sheet.

The surface of the support employed in the invention can be made hydrophilic. Known methods for making a surface of a polymer material hydrophilic such as irradiation of ultraviolet rays, glow discharge treatment, irradiation of electron radiation, chemical etching can be applied.

The support generally has a thickness in the range of approx. 50 to 500 $\mu$m, preferably approx. 70 to 300 $\mu$m.

On the support, the adhesive layer containing an inorganic oxide and a binder may be provided.

Examples of the inorganic oxide include silicon dioxide ($SiO_2$), such as crystal silicon dioxide, colloidal silica and methanol sicica etc., $SnO_2$, $TiO_2$, ZnO, and MgO. The inorganic oxide is usually used in the form of particles. There is no specific limitation on the size of the inorganic oxide particles, but the particles having a mean size in the range of approx. 10 $\mu$m to 20 $\mu$m are preferably employed.

The adhesive layer also contains a binder, which assists the formation of the inorganic oxide layer, and serves, in combination with the inorganic oxide, to enhance the adhesion between the plastic material support and the electrophoresis medium layer.

The film-forming polymer is preferably used as the binder. There is no specific limitation on the polymer, and accordingly both water-soluble polymer and water-insoluble polymer may be employed. Examples of the preferable polymer include cellulose, cellulose derivatives (e.g., nitrocellulose, diacetylcellulose and triacetylcellulose), dextran, agarose, polyacrylamide, polyvinyl alcohol ester (e.g., polyvinyl acetate), polyacrylate ester (e.g., poly-[hydroxyethylacrylate]), pullulan and pullulan derivatives.

The weight ratio between the inorganic oxide and the binder contained in the adhesive layer is in the range of approx. 1:5 to 15:1, preferably approx. 1:3 to 10:1. The adhesive layer generally has a thickness of approx. 0.1 to 30 $\mu$m, preferably approx. 0.2 to 15 $\mu$m.

On the underside (the support side) of the adhesive layer, a polymer layer can be provided. A thin layer (thickness: 0.1 to 3 $\mu$m.) of the same polymer as the binder polymer employed in the adhesive layer is preferably used as the polymer layer.

The aqueous gel medium layer is now described in more detail.

The aqueous gel medium (may be referred to herein as "gel membrane") employed in the invention is a medium layer consisting essentially of an aqueous polyacrylamide gel formed by crosslinking polymerization of an acrylamide compound and a crosslinking agent in the presence of water.

For the preparation of the polyacrylamide gel membrane, an acrylamide compound and a crosslinking agent are dissolved or dispersed in water to prepare an aqueous solution or an aqueous dispersion, in which the crosslinking reaction is carried out to form an aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous medium" is used to include both a simple water as well as an aqueous mixture of water and an organic solvent, the organic solvent being optionally added.

Examples of the acrylamide compound employable in the present invention include acrylamide and its homologues such as N-methylacrylamide, N,N-dimethylacrylamide, N-(hydroxymethyl)acrylamide and diacetonacrylamide, as well as methacrylamide and its homologes. These compounds can be employed independently or in combination. Acrylamide is most preferred among these acrylamide compounds, and said acrylamide can be also preferably employed in combination with one or more of other acrylamide compounds.

As the crosslinking agent employable to obtain the polyacrylamide gel membrane, a known crosslinking agent described, for instance, in "Electrophoresis" 1981, 2, 213-228 can be employed singly or in combination. Examples of the crosslinking agent include bifunctional compounds such as N,N'-methylenebisacrylamide (BIS), N,N'-propylenebisacrylamide (PBA), di(acrylamide dimethyl)ether (i.e., N,N'-oxydimethyleneacrylamide), 1,2-diacrylamide ethyleneglycol (DEG), 1,3-diacryloylethyleneurea, ethylene diacrylate (EDA), N,N'-diallyltartardiamide (DATD), and N,N'-bisacrylylcystamine (BAC). Examples of the crosslinking agent also include trifunctional compounds such as 1,3,5-triacryloylhexahydro-s-triazin, triallylcyanurate, triallylisocyanaurate.

The crosslinking agent can be employed in the amount of approx. 0.1 to 30 wt.%, preferably approx. 1 to 10 wt.%, based on the total weight of the monomer (i.e., acrylamide compound) and the crosslinking agent. The gel concentration preferably is in the range of approx. 3 to 30 wt/v % (total weight of monomer and crosslinking agent per total volume of gel membrane comprising monomer, crosslinking agent and aqueous medium), the concentration being expressed in accordance with the diffinition indicated by S. Hjerten in Arch. Biochem. Biophys. 1 (Suppl.), 147 (1962).

The element for electrophoresis of the present invention can be employed for analysis of proteins and conjugated proteins (e.g., lipoproteins, glycoproteins, etc.) and the medium (gel membrane) of the element may comprise an anionic surfactant as a modifier. The use of the anionic surfactant is generally essential or preferable for the electrophoretic analyses of proteins or conjugated proteins, because it contributes to perform separation of the protein and conjugated protein and determination of molecular weight of these proteins. However, the medium of the element for electrophoresis may not contain the anionic surfactant.

Examples of the anionic surfactant include alkylsulfates, particularly alkylsulfates having a long chain alkyl group of at least 10 carbon atoms. The cation contained for formation of the salt generally is an alkali metal ion such as sodium ion, potassium ion, or lithium ion. Sodium ion is preferred from the economical viewpoint. The alkylsulfates preferably are dodecylsulfates (salts of sodium, potassium, lithium, etc.), and particularly preferred is sodium dodecylsulfate (SDS). The introduction of SDS into the gel membrane is particularly advantageous for separation of proteins and conjugated protiens, as well as for determination of molecular weight thereof. The anionic surfactant (modifier) can be contained in the gel-forming solution in the amount of approx. 0.05 to 2.0 wt/v % (weight per volume of the gel-forming solution), preferably approx. 0.1 to 1.5 wt/v %.

The element for electrophoresis of the invention also can be employed for determination of base sequence of DNA, RNA, their fragments, and their derivatives. For this purpose, a compound containing at least one carbamoyl group is generally incorporated into the electrophoresis medium as a modifier. Examples of the modifier include urea and formamide. Urea is most preferred. The modifier can be used in an amount of approx. 40 to 60 wt.% based on the volume of the aqueous gel containing the monomer and crosslinking agent. In the case that urea is used as the modifier, the amount generally ranges from approx. 6 moles (approx. 360 g.) per one liter of the aqueous gel containing the monomer and crosslinking agent to the saturation amount, preferably from approx. 7 moles (approx. 420 g.) to the saturation amount.

The gel membrane of the invention may contain an oxidation inhibitor. The oxidation inhibitor can be chosen from various compounds heretofore known as oxidation inhibitors employable for the gel membrane for electrophoresis. Examples of the oxidation inhibitor include 1,4-dithiothreitol and 2-mercaptoethanol.

The gel membrane of the invention may contain a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in a range of approx. 2 to 100 wt.%, preferably, approx. 5 to 50 wt.%, based on the total weight of the monomer and crosslinking agent.

The addition of a water-soluble polymer serves to impart elasticity to the gel membrane, and thus modified gel membrane is still elastic even if it is dried. Thus the gel membrane is so improved as to be free from brittleness, whereby the gel membrane becomes hardly breakable. Further, the viscosity of the gel membrane can be controlled by selecting the molecular weight and amount of the water-soluble polymer.

The gel membrane preferably contains agarose. There is no specific limitation on the agarose to be contained in the gel membrane, and any type of agarose such as low-electroendosmosis agarose, medium-electroendosmosis agarose, or high-electroendosmosis agarose can be used. Examples of agarose employable in the invention include agaroses disclosed in Japanese Patent Provisional Publication Nos. 55(1980)-5730, 55(1980)-110946 (corresponding to U.S. Pat. No. 4,290,911 and GB 2 042 571A), 57(1982)-502098 (WO 82/02599, U.S. Pat. No. 4,319,976), etc. The amount of agarose to be added ranges from approx. 0.1 to 2 wt/v %, preferably from approx. 0.3 to 1.2 wt/v %, based on the volume of the aqueous gel containing the monomer and crosslinking agent. It becomes possible by the addition of agarose that the viscosity of the gel-forming solution can be controlled through changing the temperature of the solution, whereby suppressing flowability of the solution as well as facilitating the formation of the gel membrane.

A pH buffer agent can be contained in the gel membrane of the invention.

In the gel membrane of the element for electrophoreis of protein and protein derivatives, a buffer agent which is able to buffer a solution to a range of pH 2.5 to 10.0 can be incorporated. Such buffer agents are described in publications such as "Chemistry Handbook, Fundamental Edition" compiled by The Chemical Society of Japan (Maruzen Ltd., Tokyo, 1966) pages 1312-1320; "Modern Electrophoresis" editted by Aoki and Nagai (Hirokawa Shoten, 1973), pages 320-322; "Data for Biochemical Research" compiled by R.M.C. Dawson et al., second edition (Oxford at the Clarendon Press, 1969) pages 476-508; "Biochemistry" 5, 467 (1966); and "Analytical Biochemistry" 104, pages 300-310 (1966). Examples of the buffer agent include a buffer agent containing barbital, a buffer agent containing tris(hydroxymethyl)aminomethane (Tris), a buffer agent containing phosphate, a buffer agent containing borate, a buffer agent containing acetic acid or acetate, a buffer agent containing citric acid or citrate, a buffer agent containing lactic acid or lactate, and a buffer agent containing glycine; as well as N,N-bis(2-hydroxyethyl)glycine (Bicine), N-2-hydroxyethylpiperazine-N'-2-hydroxypropane-3-sulfonic acid (HEPPSO) or its salt, N-2-hydroxyethylpiperazine-N'-3-propanesulfonic acid (EPPS) or its salt, N-[tris(hydroxymethyl)methyl]-3-aminopropanesulfonic acid (TAPS) or its salt. Preferably examples of the buffer agent include potassium dihydrogenphosphate-disodium hydrogenphosphate, Tris-sodium borate, Tris-sodium borate-EDTA.2Na, Tris-citric acid, sodium barbital-sodium acetate, sodium barbital-hydrochloric acid, barbital-sodium barbital, acetic acid-sodium acetate, lactic acid-sodium lactate, citric acid-disodium hydrogenphosphate, Bicine, HEPPSO, sodium salt of HEPPSO, EPPS, sodium salt of EPPS, TAPS, sodium salt of TAPS, etc.

In the gel membrane of the element of electrophoresis of DNA and the like, a buffer agent which is able to buffer a solution to a range of pH 8.0 to 9.0, preferably pH 8.2 to 8.3 can be incorporated. Such buffer agents are described in the aforementioned publications.

Examples of the buffer agent include tris(hydroxymethyl)aminomethane (Tris), N,N-bis(2-hydroxyethyl)glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroxymethyl)methyl]-3-aminopropanesulfonic acid (TAPS) or its Na or K salt; as well as an acid, an alkali, and a salt empolyable in combination with the compounds. Preferable examples of the buffer agent include Tris, boric acid-EDTA.2Na (pH 8.3).

The gel membrane of the element of the invention is formed by radical crosslinking polymerization between the monomer such as acrylamide with the bi- or trifunctional compound (crosslinking agent) in an aqueous medium in which the water soluble polymer and agarose preferably are dissolved almost homogeneously.

Thus obtained gel is assumed to have a structure in which the water-soluble polymer and agarose are dispersed in the three dimensional crosslinked polymer formed by the reaction of the monomer and cross-linking agent, and the water-soluble polymer and agarose dispersed and entangle with the three dimensionally crosslinked polymer structure.

The crosslinking polymerization can be initiated by a known method, for instance, in the presence of a peroxide and/or under irradiation of ultraviolet rays. The reaction can be further accelerated by heat and irradiation with ultraviolet rays.

As the polymerization catalyst, a known low temperature-polymerization initiator such as those described in "Electrophoresis" 1981, 2, 213-219, ibid. 1981, 2, 220-228; and "Modern Electrophoresis" editted by Aoki and Nagai (Hirokawa Shoten, 1973) can be used. Examples of the initiator include a mixture of $\beta$-dimethylaminopropionitrile (DMAP) and ammonium peroxodisulfate, a mixture of N,N,N',N'-tetramethylethylene diamine (TEMED) and ammonium peroxodisulfate, a mixture of TEMED and riboflavin, a combination of a mixture of TEMED, riboflavin and hydrogen peroxide, and irradiation with ultra-violet rays. The radical reaction initiator can be employed in the amount of approx. 0.3 to 5 wt. %, preferably approx. 0.5 to 3 wt. %, based on the total amount of the monomer and crosslinking agent.

A polyol compound such as glycerol or ethylene glycol can be contained in the aqueous gel membrane of the element of the invention as a wetting agent. The polyol compound can be introduced in an amount of approx. 5 to 40 wt.% based on the volume of the aqueous gel membrane. Glycerol is particularly preferable among the polyol compounds. The addition of the wetting agent serves to keep the gel membrane from excessive dryness possibly caused by evaporation of water during storage of the medium, thereby preventing the medium from turning brittle or cracking casued by the excessive dryness. Thus, the improvement of physical properties of the gel membrane is accomplished.

The gel membrane of the element of the invention can be prepared by a process in which a gel forming solution is coated by a known method on an electric insulation support. The support may have the adhesive layer containing an inorganic oxide and a binder thereon. The gel forming solution is then crosslinked to ppolymerization on the surface of the support.

In the case the gel forming solution is crosslinked on the surface of the support, the surface of the gel forming solution layer can be covered with a plastic material covering film (including sheet and plate). The same material as employable for the plastic material support can be employed as the plastic material covering film. The plastic material covering film may be previously so treated by glow discharge treatment to have a hydrophilic surface. The plastic material covering film has a thickness of not more than 300 $\mu$m, and preferably has approx. 4 to 200 $\mu$m, from the practical viewpoint.

Thus the element for electrophoresis consisting of a plastic material support, an adhesive layer containing an inorganic oxide and a binder, a medium layer for electrophoresis and a plastic material covering film can be prepared.

The adhesive layer may be provided between the plastic material support and the medium layer for electrophoresis (the first embodiment of the invention). The adhesive layer may be also provided between the medium layer for electrophoresis and the plastic material covering film (the second embodiment of the invention). Further the adhesive layer may be provided both between the plastic material support and the medium layer for electrophoresis and between the medium layer for electrophoresis and the plastic material covering film (the third embodiment of the invention).

In the second and third embodiments, the adhesive layer on the plastic material covering film can be prepared in the same manner as in the above-described preparation of the adhesive layer on the plastic material support except that the plastic material covering film is used instead of the plastic material support. Namely, the element of the present invention can be prepared by the following steps: on the plastic material covering film is formed an adhesive layer, and then a support is provided on the gel medium layer. The element of the present invention can be also prepared by the following steps: on the plastic material support is formed an adhesive layer, the gel forming solution is coated on the adhesive layer and crosslinked thereon to form the desired gel medium layer, and then a support having another adhesive layer is provided on the gel medium layer.

The element for electrophoresis of the invention can be employed for the horizontal or vertical electrophoresis, disc electrophoresis, etc. by known methods described, for instance, in the aforementioned texts.

The medium for electrophoresis provided to the element of the present invention is strongly bound to the support through the provision of the specific adhesive layer. Accordingly, the element for electrophoresis of the present invention is always kept in the form of an integrated unit in the course of ordinary procedures. For this reason, the complicated procedures conventionally required in the electrophoresis of proteins, conjugated proteins, DNA, DNA cleavage products, etc. can be simplified by the use of the element for electrophoresis according to the present invention.

The present invention will be more clearly understood with reference to the following examples.

EXAMPLE 1

A surface of a colorless transparent polyethylene terephthalate sheet (thickness 180 μm) was made hydrophilic by irradiation of ultraviolet rays. On the surface of the sheet (support) was coated a coating solution set forth in Table 1 (coated solid amount: approx. 0.5 ml/m$^2$). The coated layer was dried at approx. 110° C. to give an adhesive layer containing an inorganic oxide and a binder.

TABLE 1

| (Composition of Coating Layer for Adhesive Layer) | | | | | |
|---|---|---|---|---|---|
| Sample No. | 1 | 2 | 3 | 4 | 5 |
| Colloidal silica (g.) | 5 | 80 | 80 | — | 80 |
| Titanium dioxide (g.) | — | — | — | 80 | — |
| Polyacrylamide (g.) | — | 10 | — | — | — |
| Nitrocellulose (g.) | 10 | — | 10 | 10 | — |
| Acetylcellulose (g.) | — | — | — | — | 10 |
| Methanol (l) | 1.1 | 0.9 | 1.1 | 1.1 | 1.1 |
| Water (l) | 0.7 | 0.9 | 0.7 | 0.7 | 0.7 |

In Table 1, colloidal silica is "Snowtex C" produced by "Nissan Kagaku Ltd." having a mean particle size in the range of 10 to 20 nm, and the above values are calculated as the solid component. Titanium dioxide is in rutile-type particles having a mean particle size in the range of 0.25 to 0.40 μm, which has no surface treatment.

On the adhesive layer provided on the surface of the support was formed a polyacrylamide gel membrane of 0.5 mm thick by coating an aqueous solution containing 9.5 g. of acrylamide, 0.5 g. of BIS, 3.58 g. of disodium hydrogenphosphate 12 hydrates, 0.33 g. of sodium dihydrogenphosphate 2 hydrates, and 0.10 g. of sodium dodecylsulfate (SDS) in 100 ml volume after addition of 1.3 ml of ammonium peroxodisulfate (5 weight %) and 33 μl of TEMED, both being the polymerization initiator. Thus, the elements consisting of the support and the polyacrylamide gel membrane thereon (Samples No. 1 to 5) were obtained.

The same procedure was repeated except that the adhesive layer was not provided on the support. Thus, an element for comparison (Comparison Sample) consisting of the support and the polyacrylamide gel membrane thereon was prepared.

The gel membrane was pushed with a finger to examine the adhesiveness between the gel layer and the support. The Samples No. 1 to 5 according to the invention showed satisfactory adhesiveness, while the Comparison Sample was poor in the adhesion.

EXAMPLE 2

A surface of a colorless transparent polyethylene terephthalate sheet (thickness 180 μm) was made hydrophilic by irradiation of ultraviolet rays. On the surface of the sheet (support) was formed a polyacrylamide gel membrane of 0.5 mm thick by coating an aqueous solution containing 9.5 g. of acrylamide, 0.5 g. of 1,3,5-triacryloylhexahydro-s-triazine, 0.3 g. of agarose (low-electroendosmosis, gelling temperature 36° C.), 2.5 g. of polyacrylamide, 3.58 g. of disodium hydrogenphosphate 12 hydrates, 0.33 g. of sodium dihydrogenphosphate 2 hydrates, and 0.10 g. of SDS in 100 ml volume after addition of 1.3 ml of ammonium peroxodisulfate (5 wt. %) and 33 μl. of TEMED, both being the polymerization initiator. Thus, the element consisting of the support and the polyacrylamide gel membrane thereon was obtained. Then a slot for sample inlet was formed at the end of the gel membrane in the conventional manner.

The same procedure as in Example 1 was repeated to obtain a covering film coated with the adhesive layer. Then the above element was covered with the covering film having the adhesive layer. Thus, the elements for electrophoresis according to the invention (Samples No. 1 to 5) were prepared.

Another element was covered directly with the covering film having no adhesive layer. Thus, an element for comparison (Comparison Sample) was prepared.

A control (standard) protein was electrophoresed on the polyacrylamide gel membrane. The element was then immersed in an aqueous Coomasie Blue R-250 (Colour Index Constitution No. 42660) solution (0.1%) for dyeing. In the dyeing process, the adhesiveness between the support and the polyacrylamide gel membrane was observed.

The gel membrane of the comparison sample completely separated immediately after the element was immersed in the dyeing solution.

The gel membranes of the Samples No. 1 to No. 5 (according to the present invention) were completely bound to the supports during the dyeing process. No unsatisfactory results were observed in the electrophoresis in the use of said element.

EXAMPLE 3

A PET covering film having an adhesive layer was prepared in the same manner as in Sample No. 3 of Examples 1. On the adhesive layer was formed a polyacrylamide gel membrane of 1 mm thick by coating an aqueous solution containing 5.7 g. of acrylamide, 0.30 g. of BIS, 1.08 g. of tris(hydroxymethyl)aminomethane [CAS Registry No. 77-86-1], 0.55 g. of boric acid, 93 mg of EDTA.Na salt and 20 g. of glycerol in 100 ml volume after addition of 1.3 ml of ammonium peroxodisulfate (5 weight %) and 33 µl of TEMED, both being the polymerization initiator, and causing the polymerization reaction in a nitrogen atmosphere. Thus, an element for electrophoresis was obtained.

A comparison sample was obtained by forming the polyacrylamide gel membrane directly on the PET sheet.

Plasmid pBR-322 of Escherichia coli was treated by a restriction enzyme AsuI and then resolved on the gel membrane of the above element. The element was then dyed with ethidium bromide. In the dyeing process, the adhesiveness between the support and the polyacrylamide gel membrane, and the DNA resolved pattern on the membranes were observed.

The gel membrane of the comparison sample completely separated immediately after the element was immersed in the dyeing solution.

The gel membranes of the Sample (according to the present invention) was completely bound to the supports during the dyeing process. No unsatisfactory result of dyed pattern on the gel membrane was observed in the electrophoresis.

EXAMPLE 4

The PET support having an adhesive layer was prepared in the same manner as in Sample No. 3 of Example 1. The PET covering film having an adhesive layer was also prepared in the same manner as in Sample No. 3 of Examples 1.

On the adhesive layer of the support was coated a gel forming solution containing the components described in Example 2 to form the gel membrane. Then the gel membrane of the support was covered with the covering film having the adhesive layer. Thus, the element for electrophoresis according to the invention was prepared.

Another element was covered directly with the covering film having no adhesive layer. Thus, an element for comparison (Comparison Sample) was prepared.

A control (standard) protein was electrophoresed on the polyacrylamide gel membrane. Then the support of the element according to the invention was easily removed, while the support base of the element for comparison could not be removed.

The gel membrane adhering to the covering film obtained by above process was then immersed in an aqueous Coomasie Blue R-250 (Colour Index Constitution No. 42660) solution (0.1%) for dyeing. In the dyeing process, the gel membrane was completely bound to to the covering film. No unsatisfactory result was observed in the electrophoresis in the use of said element.

As described above, according to this invention, it is possible to relatively change each adhesiveness of the adhesive layers between the support or the covering film and the gel membrane, so that it is also possible to optionally control the adhesiveness between the support or the covering film and the gel membrane. Thus the element for electrophoresis according to the invention has the advantage in the process for electrophoresis.

EXAMPLE 5

On the adhesive layer which was provided on the surface of the PET support using the adhesive layer composition set forth in Table 1 of Example 1 was formed a polyacrylamide gel membrane of 0.5 mm thick by coating an aqueous solution containing 11.87 g. of acrylamide, 630 mg. of BIS, 42 g. of urea, 0.55 g. of boric acid, 93 mg of EDTA.Na salt and 20 g. of glycerol in 100 ml volume after addition of 1.3 ml of ammonium peroxodisulfate (5 wt.%) and 33 µl of TEMED, both being the polymerization initiator. Thus, elements for electrophoresis were obtained.

Thus, the elements consisting of the support and the polyacrylamide gel membrane thereon (Samples No. 1 to 5) were obtained.

The same procedure was repeated except that the provision of the adhesive layer was not provided on the support. Thus, an element for comparison (Comparison Sample) consisting of the support and the polyacrylamide gel membrane thereon was prepared.

The gel membrane was pushed with a finger to examine the adhesiveness between the gel layer and the support. The Sample No. 1 to 5 according to the invention showed satisfactory adhesiveness, while the Comparison Samples were poor in the adhesion.

EXAMPLE 6

On the adhesive layers prepared as in Table 1 of Example 1 provided on the surface of the PET support were formed a polyacrylamide gel membrane of 0.5 mm thick by coating an aqueous solution containing 11.87 g. of acrylamide, 630 mg. of BIS, 0.3 g. of agarose (low electroendosmosis, gelling temperature 36° C.), 2.5 g of polyacrylamide, 1.08 g. of tris(hydroxymethyl)aminomethane [CAS Registry No. 77-86-1], 0.55 g. of boric acid and 93 mg of EDTA.Na salt in 100 ml volume after addition of 1.3 ml of ammonium peroxodisulfate (5 weight %) and 33 µl of TEMED, both being the polymerization initiator, and causing the polymerization reaction in a nitrogen atmosphere. Thus, the elements consisting of the support and the polyacrylamide gel membrane thereon (Samples No. 1 to 5) were obtained.

The same procedure was repeated except that the adhesive layer was not provided on the support. Thus, an element for comparison (Comparison Sample) consisting of the support and the polyacrylamide gel membrane thereon was prepared.

The gel membrane was pushed with a finger to examine the adhesiveness between the gel layer and the support. The Samples No. 1 to 5 according to the invention showed satisfactory adhesiveness, while the Comparison Samples were poor in the adhesion.

EXAMPLE 7

A surface of a colorless transparent polyethylene terephthalate sheet (thickness 180 µm) was made hydrophilic by irradiation of ultraviolet rays. On the surface of the sheet (support) was formed a polyacrylamide gel membrane of 0.5 mm thick by coating an aqueous solution containing 11.87 g. of acrylamide, 630 mg. of 1,3,5-triacryloylhexahydro-s-triazine, 0.3 g. of agarose, 2.5 g. of polyacrylamide, 1.08 g. of tris(hydroxymethyl)aminomethane, 0.55 g. of boric acid, and 93 mg of EDTA.Na salt in 100 ml volume after addition of 1.3 ml of ammonium peroxodisulfate (5 wt. %) and 33 μl. of TEMED, both being the polymerization initiator. Thus, the element consisting of the support and the polyacrylamide gel membrane thereon was obtained. Then a slot for sample inlet was formed at the end of the gel membrane in the conventional manner.

The same procedure as in Example 1 was repeated to obtain the covering film coated with the adhesive layer. Then the above element was covered with the covering film having the adhesive layer. Thus, the elements for electrophoresis according to the invention (Samples No. 1 to 5) were prepared.

A sample ($^{32}$P-DNA cleaved by Maxam-Gilbert method) was electrophoresed on the polyacrylamide gel membrane for sequencing the DNA. After the electrophoresis was complete, the support of the element was removed and then the gel membrane was immersed in an aqueous acetic acid (10%) solution for fixing the DNA. The gel membrane was dried and subjected to the conventional autoradiographic process. In such process, the gel membrane was completely bound to the support. No unsatisfactory results were observed in the electrophoresis in the use of said element.

Another element was covered directly with the covering film having no adhesive layer. Thus, an element for comparison (Comparison Sample) was prepared. It was impossible to remove the support base of the element for comparison, so that the procedure of the electrophoresis was also impossible.

EXAMPLE 8

The PET support having an adhesive layer was prepared in the same manner as in Sample No. 1 of Example 1. The PET covering film having an adhesive layer was also prepared in the same manner as in Sample No. 5 of Examples 1.

On the adhesive layer of the support was coated a gel forming solution containing the components described in Example 7 to form the gel membrane. Then a slot for sample inlet was formed at the end of the gel membrane, and the gel membrane of the support was covered with the covering film having the adhesive layer. Thus, the element for electrophoresis according to the invention was prepared.

The element was treated with the process of electrophoresis including autoradiography in the same manner as in Example 7. In such process, the gel membrane was completely bound to the support. No unsatisfactory results were observed in the electrophoresis in the use of said element.

We claim:

1. An element for electrophoresis comprising, in the following order:
   (I) a plastic material support;
   (II) an adhesive layer comprising an inorganic oxide in the form of particles and a film-forming polymer binder in a weight ratio in the range of 1:5 to 15:1;
   (III) a electrophoresis medium layer comprising an aqueous polyacrylamide gel formed by crosslinking polymerization of an acrylamide compound and a crosslinking agent in the presence of water; and
   (IV) a plastic material covering film.

2. The element for electrophoresis as claimed in claim 1, in which said medium layer contains a water-soluble polymer and agarose.

3. The element for electrophoresis as claimed in claim 1 or 2, in which said medium layer contains an anionic surfactant.

4. The element for electrophoresis as claimed in claim 1 or 2, in which said medium layer contains a compound having at least one carbamoyl group.

5. The element for electrophoresis as claimed in claim 1 or 2, in which the plastic support is a polyethylene terephthalate sheet.

6. The element for electrophoresis as claimed in claim 1 or 2, in which said inorganic oxide contained in the adhesive layer is a material selected from the group consisting of $SiO_2$, $SnO_2$, $TiO_2$, ZnO and MgO.

7. The element for electrophoresis as claimed in claim 1 or 2, in which said binder contained in the adhesive layer is a material selected from the group consisting of cellulose derivatives, dextran, agarose, polyacrylamide, polyvinyl alcohol ester, polyacrylate ester, pullulan and pullulan derivatives.

8. The element for electrophoresis as claimed in claim 3, in which said anionic surfactant is an alkylsulfate.

9. The element for electrophoresis as claimed in claim 4, in which said alkylsulfate is sodium dodecylsulfate.

10. The element for electrophoresis as claimed in claim 4, in which said compound having at least one carbamoyl group is urea or formamide.

11. The element for electrophoresis of claim 1 wherein the inorganic particles have a mean particle size from 10 to 20 μm.

12. An element for electrophoresis comprising, in the following order:
    (I) a plastic material support;
    (II) an adhesive layer comprising an inorganic oxide in the form of particles and a film forming polymer binder in a weight ratio in the range of 1:5 to 15:1;
    (III) an electrophoresis medium layer comprising an aqueous polyacrylamide gel formed by crosslinking polymerization of an acrylamide compound and a crosslinking agent in the presence of water; and
    (IV) an adhesive layer containing an inorganic oxide in the form of particles and a binder; and
    (V) a plastic material covering film.

13. The element for electrophoresis as claimed in claim 12, in which said medium layer contains a water-soluble polymer and agarose.

14. The element for electrophoresis as claimed in claim 12 or 13, in which said medium layer contains an anionic surfactant.

15. The element for electrophoresis as claimed in claim 12 or 13, in which said medium layer contains a compound having at least one carbamoyl group.

16. The element for electrophoresis as claimed in claim 12 or 13, in which the plastic support is a polyethylene terephthalate sheet.

17. The element for electrophoresis as claimed in claim 12 or 13, in which said inorganic oxide contained in the adhesive layer is a material selected from the group consisting of $SiO_2$, $SnO_2$, $TiO_2$, ZnO and MgO.

18. The element for electrophoresis as claimed in claim 12 or 13, in which said binder contained in the adhesive layer is a material selected from the group consisting of cellulose derivatives, dextran, agarose, polyacrylamide, polyvinyl alcohol ester, polyacrylate ester, pullulan and pullulan derivatives.

19. The element for electrophoresis as claimed in claim 14, in which said anionic surfactant is an alkylsulfate.

20. The element for electrophoresis as claimed in claim 19, in which said alkylsulfate is sodium dodecylsulfate.

21. The element for electrophoresis as claimed in claim 15, in which said compound having at least one carbamoyl group is urea or formamide.

22. The element for electrophoresis of claim 12 wherein the inorganic particles have a mean particle size from 10 to 20 μm.

* * * * *